(12) United States Patent
O'Donnell, Jr.

(10) Patent No.: US 7,452,330 B2
(45) Date of Patent: *Nov. 18, 2008

(54) COMBINED APPLANATION TONOMETER AND ULTRASONIC PACHYMETER

(75) Inventor: Francis E. O'Donnell, Jr., St. Louis, MO (US)

(73) Assignee: SUBLASE, Inc., Rydal, PA (US)

( * ) Notice: Subject to any disclaimer, the term of this patent is extended or adjusted under 35 U.S.C. 154(b) by 587 days.

This patent is subject to a terminal disclaimer.

(21) Appl. No.: 10/234,294

(22) Filed: Sep. 3, 2002

(65) Prior Publication Data

US 2004/0044278 A1  Mar. 4, 2004

(51) Int. Cl.
*A61B 3/16* (2006.01)
(52) U.S. Cl. .................................... 600/399
(58) Field of Classification Search ......... 600/398–405, 600/561
See application file for complete search history.

(56) References Cited

U.S. PATENT DOCUMENTS

| | | | | |
|---|---|---|---|---|
| 3,597,964 A | * | 8/1971 | Heine et al. | 600/405 |
| 3,832,891 A | * | 9/1974 | Stuckey | 600/405 |
| 3,977,237 A | * | 8/1976 | Tesi | 600/405 |
| 5,070,875 A | * | 12/1991 | Falck et al. | 600/405 |
| 5,203,331 A | * | 4/1993 | Draeger | 600/405 |
| 5,474,066 A | * | 12/1995 | Grolman | 600/398 |
| 5,636,635 A | | 6/1997 | Massie et al. | |
| 6,113,542 A | * | 9/2000 | Hyman et al. | 600/398 |
| 6,440,070 B2 | * | 8/2002 | Israel | 600/398 |
| 6,776,756 B2 | * | 8/2004 | Feldon et al. | 600/405 |

* cited by examiner

*Primary Examiner*—Max Hindenburg
*Assistant Examiner*—Fangemonique Smith
(74) *Attorney, Agent, or Firm*—Drinker Biddle & Reath LLP

(57) ABSTRACT

An improved apparatus and method of intraocular pressure determination is disclosed in which applanation tonometry is done with an ultrasonic transducer. The method allows for increased accuracy of intraocular pressure determination based upon adjustment of applanation tonometry for subjacent corneal thickness. The device allows for the operator to view the corneal surface and the pattern of dye to determine the precise endpoint of applanation.

13 Claims, 3 Drawing Sheets

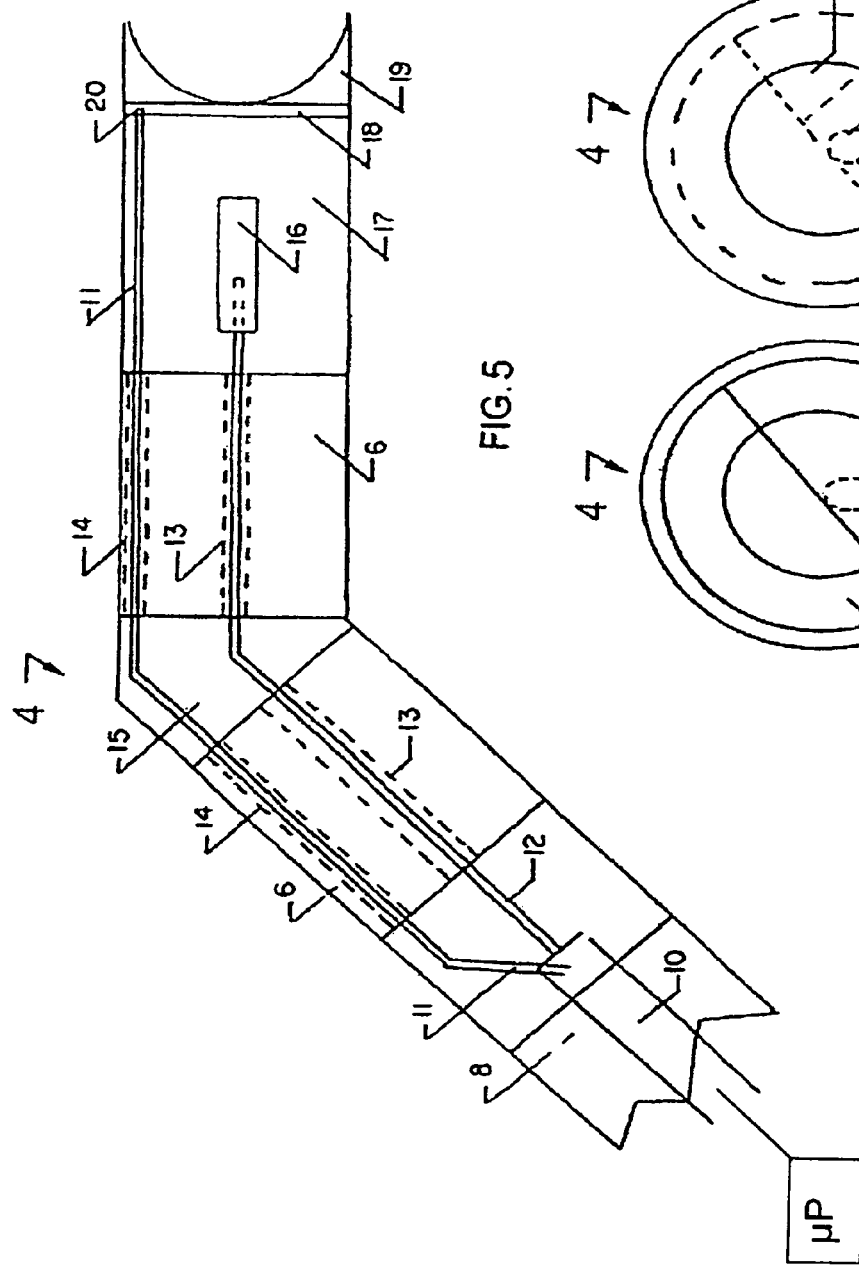
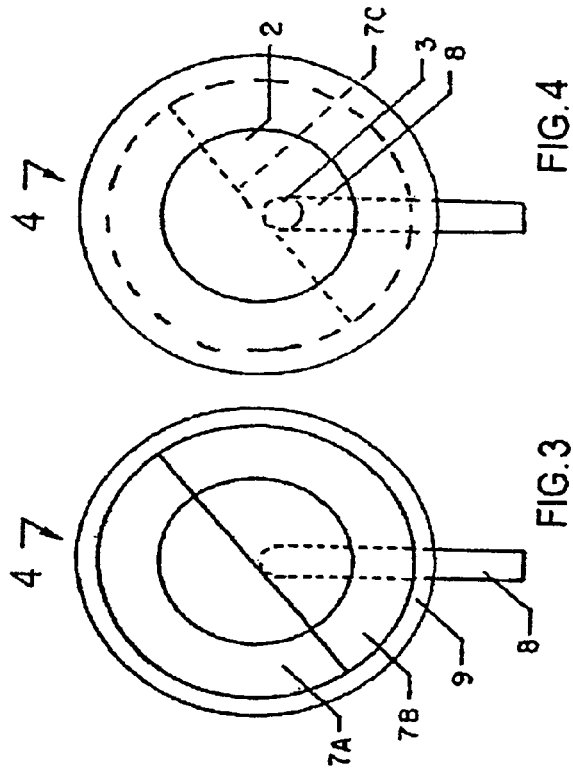
FIG. 3
FIG. 4
FIG. 5

COMBINED APPLANATION TONOMETER AND ULTRASONIC PACHYMETER

FIELD OF THE INVENTION

The present invention uses a novel applanation tonometer to measure intraocular pressures for the purposes of diagnosing and monitoring treatment for glaucoma. Specifically, the applanation is done with an ultrasonic transducer which measures the corneal thickness at the exact point of applanation. Since applanation pressure is a function of corneal thickness, the simultaneous determination of both allows for more accurate determination of intraocular pressure. The configuration of the applanating component allows for internal reflection giving the operator the ability to see better the corneal surface allowing for atraumatic contact with the delicate cornea and to see better the pattern of the imaging dye used to determine the precise endpoint of applanation.

BACKGROUND OF THE INVENTION

Applanation tonometry was popularized by Goldmann as an improved method of intraocular pressure determination in comparison to indentation tonometry. The principal of Goldmann's applanation tonometry is based upon the Imbert-Fick principle, which teaches that the pressure inside a liquid-filled sphere can be determined by measuring the force required to flatten a portion of the surface. It will be obvious to one knowledgeable about the art that variations in thickness of the cornea would affect the accuracy of its applanation in the Goldmann technique. Specifically, a thinner than normal cornea would applanate easier than a normal thickness cornea, thereby generating a falsely low measure of intraocular pressure. Conversely, a thicker cornea than normal would overestimate the true intraocular pressure. Since the diagnosis of glaucoma and the assessment of the adequacy of treatment is largely dependent on intraocular pressure, the accuracy of intraocular pressure measurement is of paramount importance. In order to compensate for variations in corneal thickness, prior art has used pachymetry by optical or ultrasonic means to measure corneal thickness. It is time-consuming and expensive to use a second machine (e.g. ultrasonic pachymetry) sequentially. Moreover, it was impossible to know if the portion of cornea applanated for tonometry was the portion whose thickness was measured. Finally, the determination of both applanation tonometry and corneal pachymetry required solving an equation in order to identify the true intraocular pressure. As a result, the correction of applanation tonometry for corneal thickness variables is not generally done except in research circumstances. Recently, studies of ocular hypertensive patients have demonstrated that corneal thickness is the single most important predictor of glaucoma. Corneal thickness is inversely proportional to the risk of developing glaucomatous damage. That is to say, among ocular hypertensives, the thinner the cornea the greater the risk of glaucoma. In U.S. Pat. No. 6,083,161, I disclosed a new apparatus and method which provides more accurate intraocular pressure determination because using a single device it measures corneal thickness at the exact point of corneal applanation, then it corrects the measured intraocular pressure for the measured corneal thickness.

During standard applanation tonometry, a fluorescein-type dye is applied to the corneal surface. The operator looks through the oculars of the slit lamp in order to get a magnified view of the applanation device. The operator views the corneal surface in the area to be applanated by viewing through the transparent applanating component. This helps to reduce inadvertent trauma to the delicate epithelial layer of the cornea. The operator determines the endpoint of applanation by identifying a predetermined pattern of fluorescein dye created when just enough contact is made with the corneal surface. This is because to measure tonometry accurately, it is important not to under-applanate or over-applanate the cornea. My prior U.S. Pat. No. 6,083,161 teaches an improved apparatus and method of intraocular pressure determination but the invention made it more difficult for the operator to view the cornea during applanation in order to avoid traumatic contact and to view the pattern of the dye for determination of the endpoint of applanation. This viewing problem was the result of the incorporation of an opaque ultrasonic transducer in the applanating component. In order to be significantly more user friendly, the present invention simultaneously measures applanation tonometry and corneal pachymetry at the same point on the cornea and it allows for preservation of the operator's ability to visualize the corneal surface and the dye pattern during measurements by means of internal reflection.

My prior U.S. Pat. No. 6,083,161, upon related and earlier technology, described an applanation apparatus which allows for the determination of applanation pressure and membrane thickness of the eye, having a fluid filled cavity, wherein a transparent transducer body having a corneal contact surface for applanation of the cornea, utilizes an ultrasonic transmitter and receiver within said transparent transducer body for sending and receiving an ultrasonic signal to said applanated cornea, with the ultrasonic signal being processed to determine the applanation pressure and the membrane thickness of the eye.

In addition, the prior patent to Massie, U.S. Pat. No. 5,636,635, discloses a tonometer, that is a non-contact tonometer, for measuring the intraocular pressure of an eye, the cornea of the eye having a generally convex surface, which includes the use of an ultrasonic transducer means, that focuses a beam of acoustic radiation on a spot on the surface of the cornea, to produce sufficient radiation pressure to temporarily distort the surface of the cornea, it also utilizes a distortion detection means for detecting that deflected change in surface, and also utilizes acoustic radiation pressure estimating means for providing a signal from which the radiation pressure on the spot can be estimated, and then includes means for correlated said signal with the distortion to estimate the intraocular pressure of the eye.

SUMMARY OF THE INVENTION

There exists a need, therefore, for a user-friendly device that can simultaneously determine tonometry and pachymetry, and which can register a more accurate intraocular pressure for general clinical use. The present invention applanates an ultrasonic transducer on the cornea, simultaneously recording applanation pressure and corneal thickness at the exact point of applanation. A microprocessor means converts the applanation pressure to an adjusted intraocular pressure which more accurately reflects the intraocular pressure than by applanation tonometry alone. This device and method allows for quick, convenient, and precise determination of intraocular pressure.

It is an object of the present invention to provide a device which can easily and accurately determine intraocular pressure regardless of variations in corneal thickness.

It is a further object of the present invention to provide pachymetry determination at the exact point of applanation of the cornea.

It is a further object of the present invention to use a microprocessor means to adjust the applanation pressure determination for corneal thickness and to record for the clinician an adjusted intraocular pressure.

It is a further object of the present invention to use an applanating component designed so as to allow the operator to view the corneal surface at the point of applanation thereby facilitating atraumatic use of the device.

It is a further object of the present invention to use an applanating component designed so as to allow the operator to view the pattern of the fluorescein dye during applanation in order to precisely determine the endpoint of applanation.

Other objects and purposes for this invention will occur to those skilled in the art upon review of the invention as described and analyzed herein, in light of its drawings.

BRIEF DESCRIPTION OF THE DRAWINGS

FIG. 3 is a rear elevational view of the transmitter/receiver assembly of the present invention;

FIG. 4 is a front elevational view of the transmitter/receiver assembly transducer of the present invention;

FIG. 5 is a side elevational view of the transmitter/receiver assembly transducer signal conveyance rod.

DESCRIPTION OF THE PREFERRED EMBODIMENT

Figure 1:
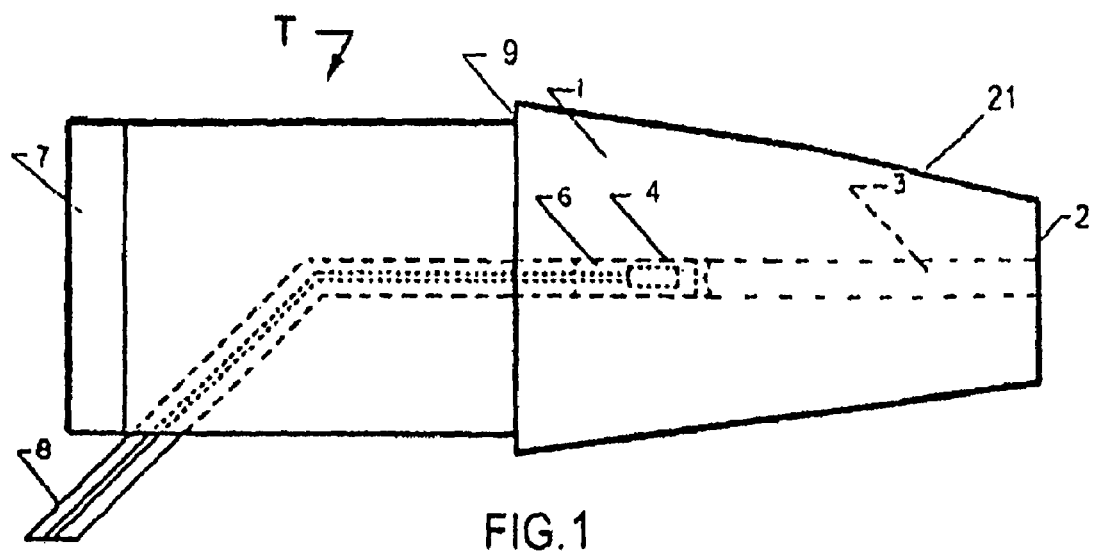
FIG. 1 is side elevational view of the tonometer/pachymeter transducer of the present invention.

It is a preferred embodiment of the present invention to use a solid-state, ultrasonic transducer head working in the 10-50 MHz domain as an applanation surface of predetermined area for contact with the corneal surface.

In another preferred embodiment, the device displays an LED of the applanation pressures, the pachymetry and the (adjusted) intraocular pressure.

In another preferred embodiment of the present invention, the transparent applanation component containing the ultrasonic transducer has one or more flat surfaces 21 which allow for total internal reflection. "Total internal reflection" is a mirror-like effect achieved by viewing a flat surface at a very acute angle 22 and it is well-known in the ophthalmic field. This mirrored effect gives the operator an unobstructed view of the area of the cornea that is applanated and a view of the pattern of the fluorescein dye in order to determine the endpoint of applanation.

The apparatus of this invention describes and shows herein a novel device for simultaneous measurement at the same locus of applanation pressure and of the surface thickness of a fluid-filled sphere for determination of intracavity pressure, wherein a portion or all of the applanating surface is an ultrasonic transducer. The method for utilizing this device includes the simultaneous measurement at the same locus of applanation pressure and of surface thickness of a fluid-filled sphere for determination of intracavity pressure. In addition this novel device provides for simultaneous measurement at the locus of applanation tonometry and of cornea pachymetry for determination of intraocular pressure, wherein a portion or the entire applanating surface is an ultrasonic transducer.

Finally, this invention includes a method of simultaneous measurement at the same locus of applanation tonometry and of cornea pachymetry for the purpose of intraocular pressure determination. Referring now to the drawings, the tonometer/pachymeter transducer of the present invention is indicated generally by reference figure T. The tonometer/pachymeter includes a transducer body 1 with a corneal contact surface 2. The corneal contact surface 2 creates the optical juncture of the cornea and the transducer body and is used to applanate or flatten a predetermined area of the anterior cornea. This allows the user to view and gauge the position and quality of contact between the cornea and transducer. The transducer body 1 is transparent and allows the user to posteriorly view the corneal contact surface 2. Within body 1 is a signal conveyance rod 3 connected to a transmitter/receiver assembly 4 which is connected to digital readout hardware (not shown) by a coaxial cable 10 housed in a coaxial cable support tube 8. The transmitter/receiver assembly 4 is aimed at the geometric center of the corneal contact surface and projects an ultrasonic signal to the corneal contact surface, through the cornea and collects the return signal from the posterior corneal surface. The ultrasonic signal is propagated from an external source (not shown) and passed to a microprocessor µP through the coaxial cable 10. The microprocessor is programmed to receive the transducer output signal and correct the signal for corneal membrane thickness to determine a true intracavity pressure. Tonometer/pachymeter transducer T also includes an opposing prism assembly 7 which has an upper prism 7A and a lower prism 7B separated by a prism delineation line 7C. The prisms are used to split the image from the corneal contact surface 2 and create a lateral disparity between the prism-induced images. The prisms are parallel to each other and positioned edge to edge and base to apex. The prisms can be orientated from zero to one hundred and eighty degrees on the posterior end of the transducer body 1. Within the body is a solid acrylic insert and wire guide 6. Body 1 also has shoulder 9 so that the tonometer/pachymeter transducer T can be rested in a conventional tonometer mount.

The arrangement of the interior elements of tonometer/pachymeter transducer T are best seen in FIG. 5 and include a shield wire 11 extending from the coaxial cable 10 and also a primary wire 12. The acrylic insert and wire guide 6 includes a drilled hole wire guide 13 for the primary wire 12 and a drilled hole wire guide 14 for the shield wire 11.

An air gap 15 is position between the two wire guides. The shield wire 11 is connected to a germanium disc 18 by solder connection 20. A signal emitter 16 is embedded in a graphite casing 17 which is glued or otherwise attached to the germanium disc 18. A silicone concave collar 19 is mated to the posterior end of the signal conveyance rod.

Figure 2:
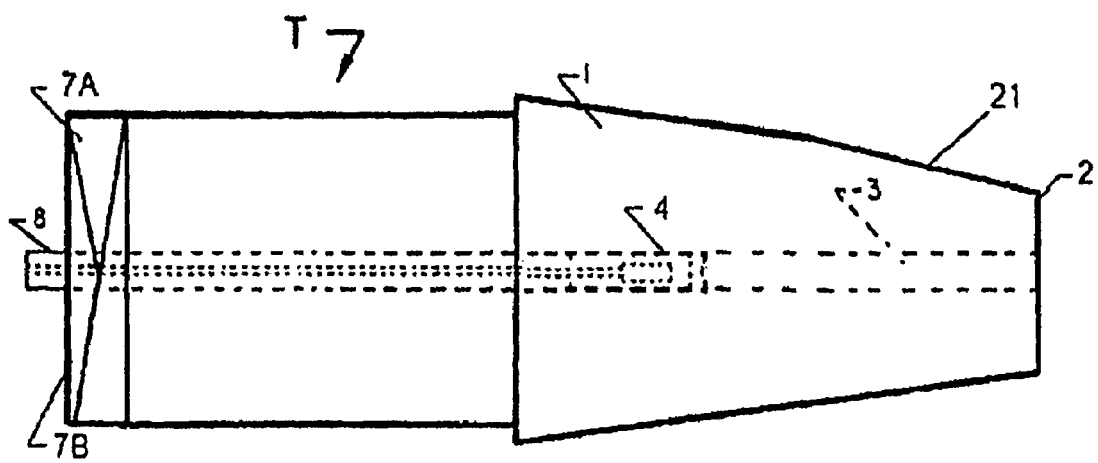
FIG. 2 is a top plan of the tonometer/pachymeter transducer of the present invention.
Figure 6:
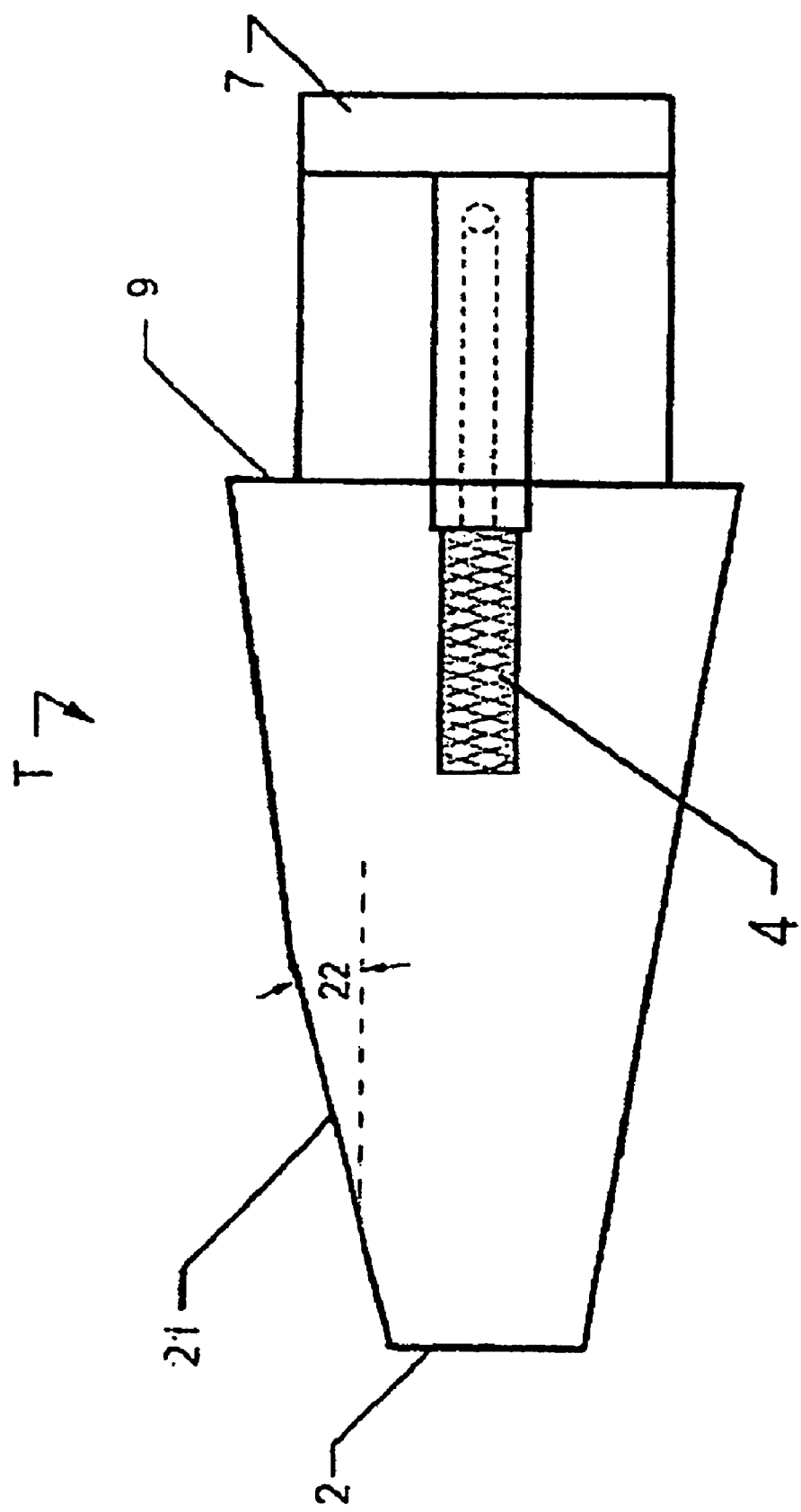
FIG. 6 is an elevational view of an alternate embodiment of the tonometer/pachymeter transducer showing the use of a flat surface on the transducer body of the present invention to achieve an internal mirror effect.

A useful embodiment of the present invention is shown in FIGS. 1, 2 and 6. By making one or more flat surfaces 21 on the sides of the applanating component, the device creates an internal, mirrored effect by total internal reflection. As may be seen from FIGS. 1, 2, and 6, the surface 21 is at an acute angle 22 to a central axis of the body 1 perpendicular to the corneal contact surface 2, and is angled away from the axis in a direction from the corneal contact surface towards the posterior end of the body 1. This mirrored effect reflects an image of the corneal contact surface 2, and of the cornea with which that surface is in contact, around the ultrasonic transmitter and receiver 5, 6 to the posterior surface at 7, and can be used by the operator to view the corneal surface during applanation in order to facilitate atraumatic contact with the corneal surface during measurements and in order to view the pattern of fluorescein dye used to determine the endpoint of applanation. Note that the transmitter/receiver assembly 4 does not need to extend all the way to the applanating surface in order to give accurate measurements of corneal thickness.

EXAMPLE 1

A patient's right eye had undergone photorefractive keratectomy for a minus ten diopters of myopia three months prior to intraocular pressure determination with the present invention. The applanation pressure as measured by a Goldmann tonometer was recorded as 17 mm Hg. The applanation pressure recorded with the present invention was 17 mm Hg. The corneal pachymetry at the applanation location on the cornea was measured as 390 microns, and the corrected intraocular pressure of the present invention was 23 mm Hg. Thus, the present invention demonstrated that the intraocular pressure was higher than would be otherwise be apparent, and most importantly, it was in a range above normal (20 mmHg.).

Variations or modifications to the subject matter of this invention may occur to those skilled in the art upon review of the summary provided herein, in addition to the description of its preferred embodiment, in light of the drawings. Such variations, if within the spirit of this invention, are intended to be encompassed within the scope of the invention as described herein.

I claim:

1. An applanation apparatus which allows for the determination of applanation pressure and membrane thickness of an eye having a fluid filled cavity comprising:
   a transparent transducer body having one or more generally longitudinal flat surfaces, a corneal contact surface for applanation of the cornea, and a posterior viewing surface opposite the corneal contact surface, the one or more generally longitudinal flat surfaces being so positioned as to enable viewing through the corneal contact surface from the posterior viewing surface by reflection in the one or more generally longitudinal flat surfaces; and,
   an ultrasonic transmitter and receiver within said transparent transducer body for sending and receiving an ultrasonic signal to said applanated cornea, said ultrasonic signal processed to determine the applanation pressure and membrane thickness of the eye.

2. The applanation apparatus of claim 1 including a microprocessor, the microprocessor capable of receiving said ultrasonic signal and a signal indicative of applanation contact pressure, said microprocessor capable of correcting said signal indicative of applanation pressure for a corneal membrane thickness to determine a true intracavity pressure independent of corneal membrane thickness.

3. The applanation apparatus of claim 2 wherein said microprocessor determines the membrane thickness at the point of applanation.

4. A method of determining intraocular pressure of a human eye comprising:
   providing a transducer including a transparent body with one or more generally longitudinal flat surfaces and a corneal contact surface at a front end, an ultrasonic transmitter and receiver within said body, said ultrasonic transmitter and receiver being in communications with a microprocessor, said microprocessor being capable of correcting an intraocular pressure signal for a corneal thickness to determine a true intraocular pressure independent of corneal thickness,
   placing the corneal contact surface of the transducer against a cornea while viewing the cornea through the corneal contact surface by means of total internal reflection in one or more said generally longitudinal flat surfaces through a viewing surface at a rear end of the transparent body;
   creating an applanation point on the cornea with said corneal contact surface;
   viewing said applanation point by means of total internal reflection in said one or more generally longitudinal flat surfaces through said viewing surface at a rear end of the transparent body,
   measuring an intracavity pressure at said applanation point with said transparent transducer body;
   measuring a corneal thickness with said ultrasonic transmitter and receiver; and,
   correcting the measured intracavity pressure for the measured corneal thickness to determine the true intraocular pressure.

5. The applanation apparatus of claim 1 further comprising an opposing prism assembly.

6. The applanation apparatus of claim 2 further comprising a signal conveyance rod between said corneal contact surface and said ultrasonic transmitter and receiver.

7. The applanation apparatus of claim 6, further comprising a signal emitter on said signal conveyance rod.

8. The applanation apparatus of claim 7, further comprising a germanium disc on said signal emitter.

9. The applanation apparatus of claim 1 wherein said ultrasonic transmitter and receiver is opaque.

10. The applanation apparatus of claim 1 wherein said flat surface is disposed at an acute angle to a longitudinal axis perpendicular to the corneal contact surface of said transparent transducer body.

11. The applanation apparatus of claim 10 wherein said flat surface reflects an image of said applanated cornea around said ultrasonic transmitter and receiver.

12. The applanation apparatus of claim 1 wherein the corneal contact surface is totally internally reflected in the one or more generally longitudinal flat surfaces as viewed from the posterior viewing surface.

13. The applanation apparatus of claim 10, wherein the longitudinal axis of said transparent transducer body passes through the posterior viewing surface.

* * * * *